(12) United States Patent
Ekeinde et al.

(10) Patent No.: US 11,849,687 B2
(45) Date of Patent: Dec. 26, 2023

(54) BIOLOGICAL POLLINIZATION SYSTEM

(71) Applicants: Alan David Odili Ekeinde, Sterling, VA (US); Augustine Odili Ekeinde, Jr., Phoenix, AZ (US)

(72) Inventors: Alan David Odili Ekeinde, Sterling, VA (US); Augustine Odili Ekeinde, Jr., Phoenix, AZ (US)

( * ) Notice: Subject to any disclaimer, the term of this patent is extended or adjusted under 35 U.S.C. 154(b) by 0 days.

(21) Appl. No.: 18/073,491

(22) Filed: Dec. 1, 2022

(65) Prior Publication Data
US 2023/0172130 A1 Jun. 8, 2023

Related U.S. Application Data

(63) Continuation of application No. 17/540,342, filed on Dec. 2, 2021.

(51) Int. Cl.
*A01H 1/02* (2006.01)
(52) U.S. Cl.
CPC .................... *A01H 1/027* (2021.01)
(58) Field of Classification Search
CPC ...... A01H 1/027; A01G 7/06; A01G 13/0206; A01G 13/0212; A01G 13/0231; A01G 13/0243; A01G 13/043; A01G 2013/046; A47G 7/085
See application file for complete search history.

(56) References Cited

U.S. PATENT DOCUMENTS

| | | | |
|---|---|---|---|
| 4,679,350 A * | 7/1987 | Banta | A01G 13/0231 47/21.1 |
| 7,866,089 B2 | 1/2011 | Wig et al. | |
| 9,968,040 B2 * | 5/2018 | Eisenhauer | A01H 1/027 |
| 2002/0134010 A1 | 9/2002 | Rohrborn, Jr. et al. | |
| 2009/0145024 A1 * | 6/2009 | Mendoza-Sosa | A01G 13/0231 47/24.1 |
| 2018/0160633 A1 | 6/2018 | DeLao | |

FOREIGN PATENT DOCUMENTS

| | | | | |
|---|---|---|---|---|
| KR | 20130073168 A * | 7/2013 | | |
| WO | WO-2005063000 A2 * | 7/2005 | ......... | A01G 13/0231 |
| WO | WO-2022192062 A1 * | 9/2022 | ............ | A01H 1/027 |
| WO | WO-2023021508 A1 * | 2/2023 | | |

\* cited by examiner

*Primary Examiner* — Trinh T Nguyen
(74) *Attorney, Agent, or Firm* — Ariel S. Bentolila; Bay Area IP Group, LLC

(57) ABSTRACT

A system including means for encapsulating a plant in a closed environment; means for injecting pollen into said closed environment; means for expanding a space covered by said closed environment; means for filtering contaminants from entering said closed environment; means for attaching said closed environment to a plant appendage or plant container; means for holding or diffusing pollen inside said closed environment; and means for maximizing an amount light penetrating within said closed environment.

19 Claims, 18 Drawing Sheets

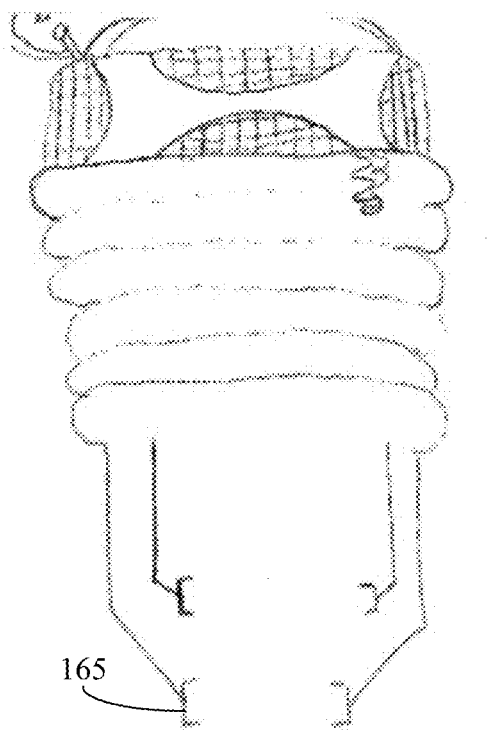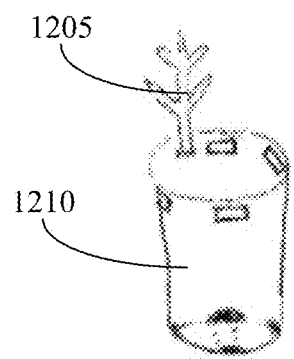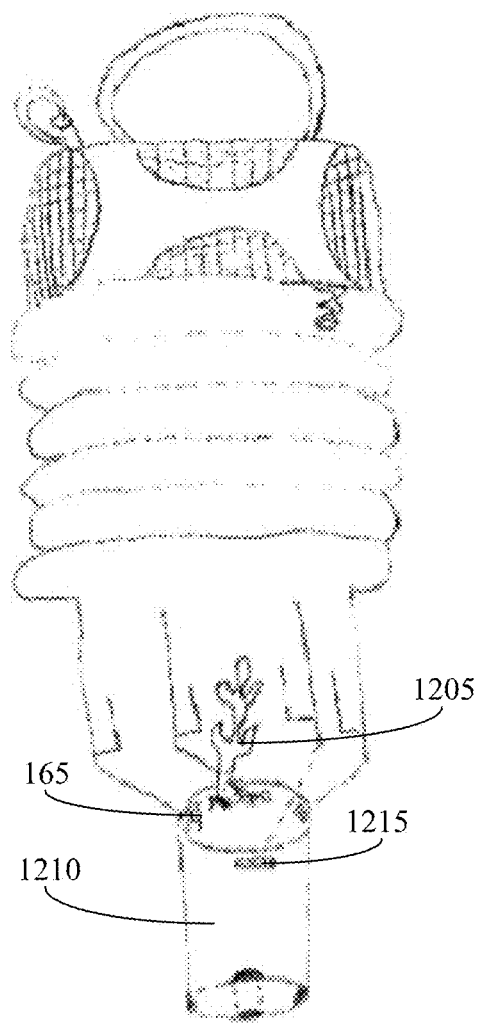
Fig. 12A            Fig. 12B

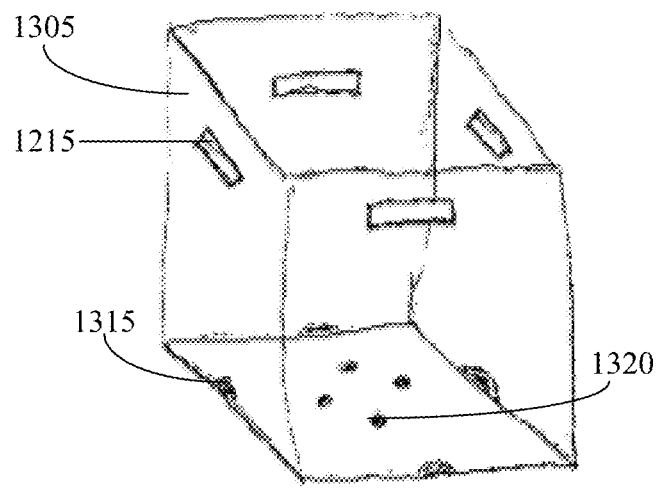
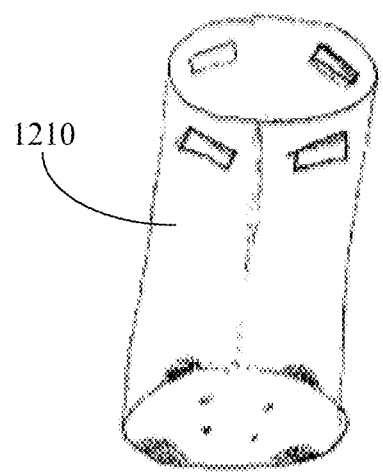
Fig. 13A   Fig. 13B
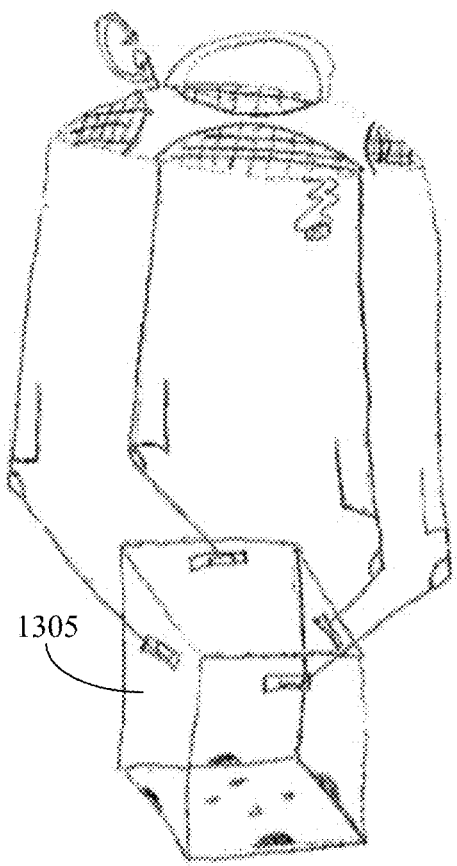
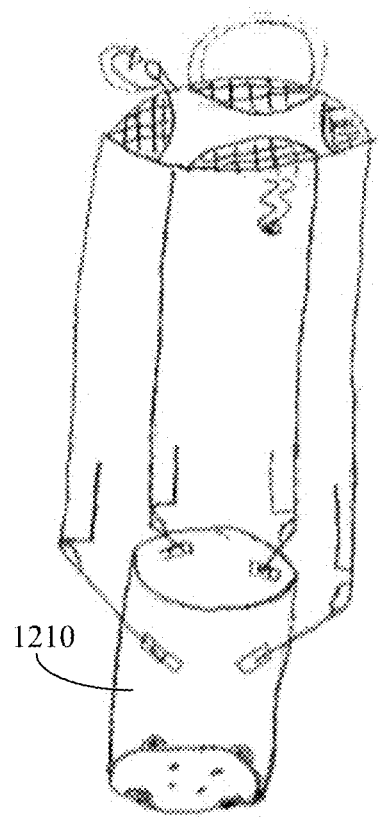
Fig. 13C   Fig. 13D

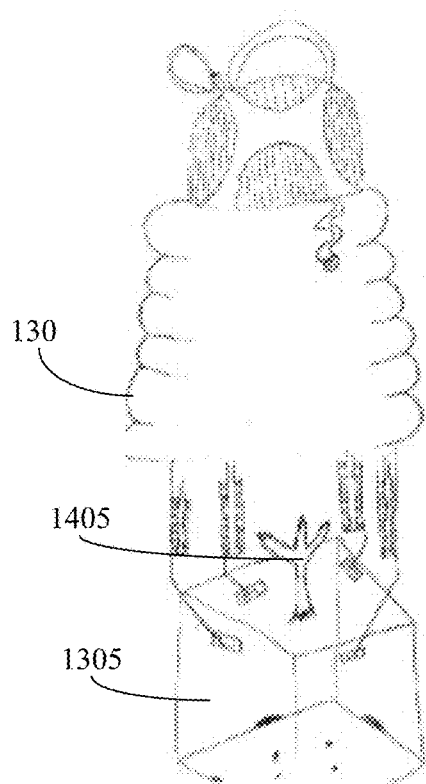
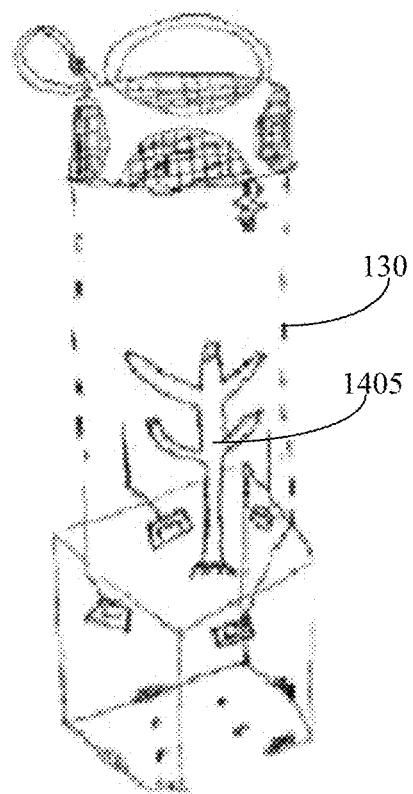
Fig. 14A        Fig. 14B
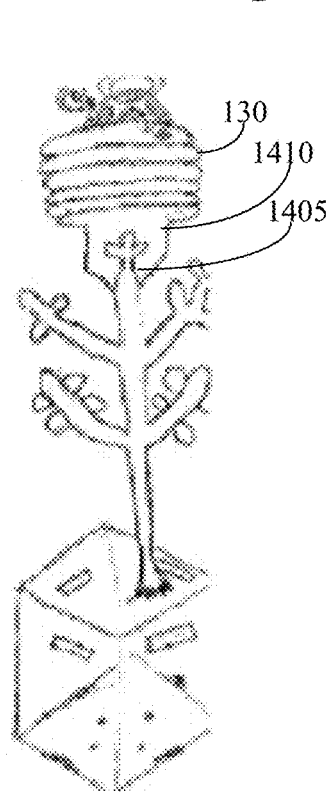
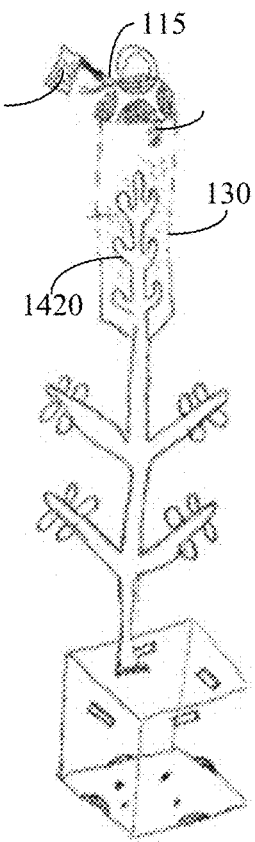
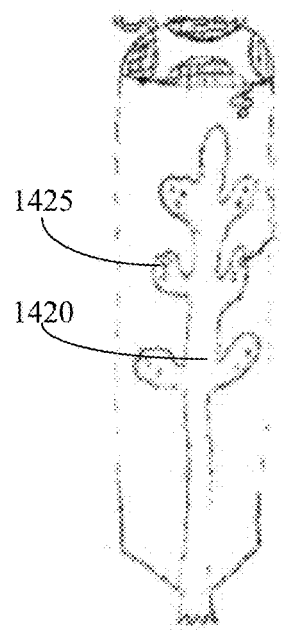
Fig. 14C        Fig. 14D        Fig. 14E

BIOLOGICAL POLLINIZATION SYSTEM

CROSS-REFERENCE TO RELATED APPLICATIONS

The present continuation patent application claims priority benefit of the U.S. nonprovisional patent application Ser. No. 17/540,642, filed on 2 Dec. 2021, titled "Biological Pollinization System" under 35 U.S.C. 120. The contents of this related patent application is incorporated herein by reference for all purposes to the extent that such subject matter is not inconsistent herewith or limiting hereof.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to plant cover apparatus. More particularly, certain embodiments of the invention relate to plant pollination systems.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that plant species may be bred for commercial purposes. For example, in some commercial applications plant species may be bred to form hybrid plant species. In some applications, hybrid plants may be bred to exhibit various desirable traits. Such traits may include, improved yield characteristics, improved agronomic quality, resistance to heat and drought, and resistance to disease and insect damage. Typically, plants may be capable of self-pollination, cross-pollination, or both. Self-pollination may include pollination using pollen from one flower that is transferred to the same or another flower of the same plant. Cross-pollination may include pollination using pollen delivered from a flower of a different plant from a different family, line, or species.

In commercial growing of trees or fruits such as pears, apples, etc., better tree or fruit set may be obtained by cross pollination. Pollen may be extracted from certain varieties of fruit trees and used to pollinate the buds of other trees by being released or dispensed in the vicinity thereof. Since pollen is expensive, it may be desirable to release pollen in a manner which provides the most efficient utilization in terms of both the amount and uniformity of the released pollen which may be ultimately effective. Prior pollen dispensing techniques include releasing pollen from low-flying aircraft, beehive inserts, firing from shotgun shells, etc. None of these prior means is entirely satisfactory since the operator cannot observe precisely where the dispensed pollen is going, and cannot control the amount of pollen dispensed in any given location.

Typical pollination processes may involve protecting plants from unwanted airborne pollen by covering it at an early stage. After the plant has reached a sufficient level of development, the plant cover may be removed and pollinates the plant with pollen from another carefully selected plant. A standard cover in the industry may be constructed with a sheet of white paper to form a thin flat tube, then folding one end over so that the tube may be closed. The standard design may be vulnerable to high winds which tend to blow it off the plant. Care must be taken in placing and checking the standard cover since it may not expand easily to allow for the growth of the plant shoot. It is not uncommon for the standard cover to burst open if the shoot becomes too large, rendering the plant useless for the purpose of hybridization. To remedy this, plant covers may be watched when ready to burst and to loosen them by sliding them upward to a certain degree. This procedure may be time consuming and may require careful observation.

With standard paper cover, it may be difficult to determine if the plant is ready for hybridization since the standard paper cover device may not permit observation of the shoot within. Therefore, it may be necessary to exposing one or more plants by removing their covers to observe the stage of development. Once the cover is removed, airborne pollen from unwanted sources may enter and the plant may be rendered unusable.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3A shows the exemplary biological pollinization system while compressed and FIG. 3B shows the exemplary biological pollinization system while expanded, in accordance with an embodiment of the present invention;

FIGS. 10A-10B illustrate exemplary feet of a biological pollinization system, wherein FIG. 10A shows the interlocking of the exemplary feet and FIG. 10B shows an exemplary foot, in accordance with an embodiment of the present invention;

FIGS. 12A-12B illustrate an exemplary biological pollinization system placed over a plant in a base, in accordance with an embodiment of the present invention;

FIGS. 13A-13D illustrate exemplary bases to be used with an exemplary biological pollinization system, wherein FIGS. 13A-13B show exemplary bases and FIGS. 13C-13D show the exemplary bases attached to the exemplary biological pollinization system, in accordance with an embodiment of the present invention;

FIGS. 14A-14E illustrate an exemplary biological pollinization system in use, in accordance with an embodiment of the present invention;

Figure 1:
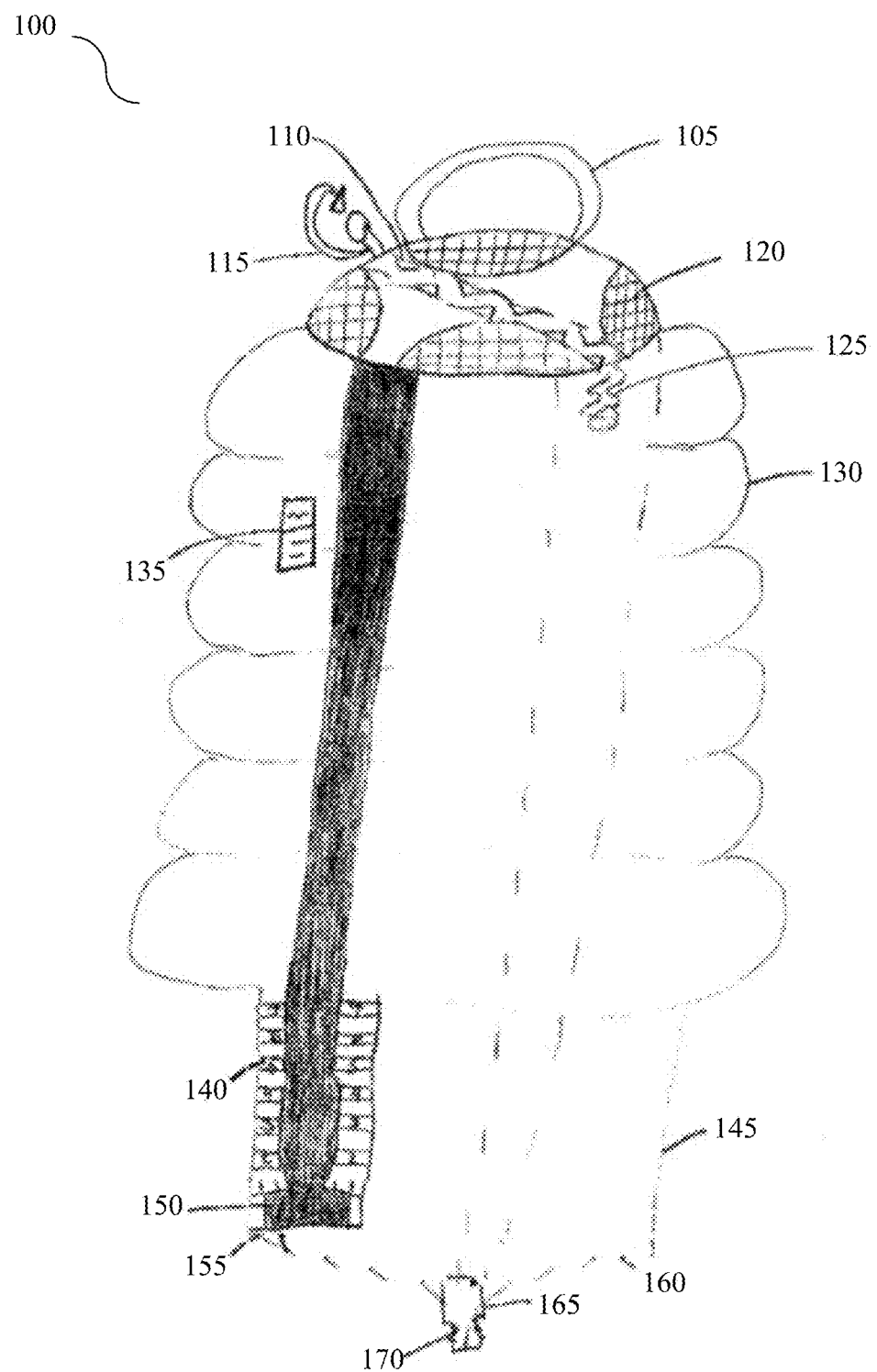
FIG. 1 illustrates an exemplary biological pollinization system, in accordance with an embodiment of the present invention.
Figure 2A:
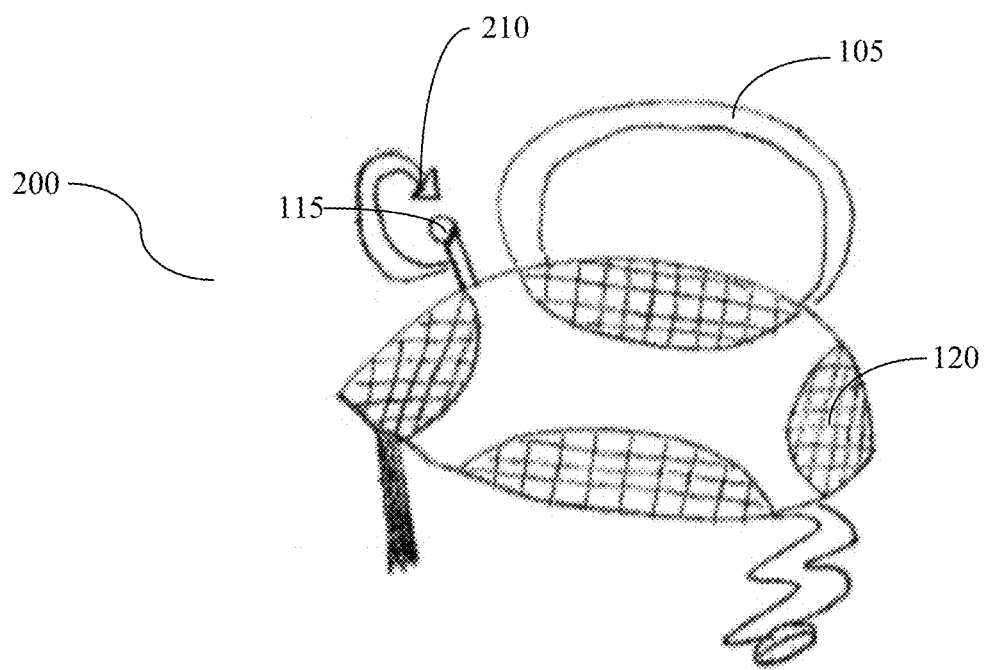
FIGS. 2A-2B illustrate an exemplary pollinization head piece, in accordance with an embodiment of the present invention.
Figure 2B:
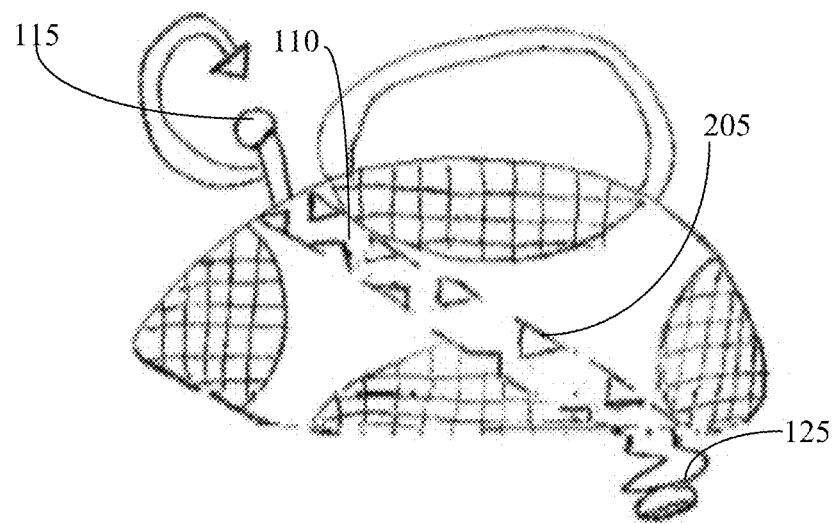
Figures 3A, 3B:
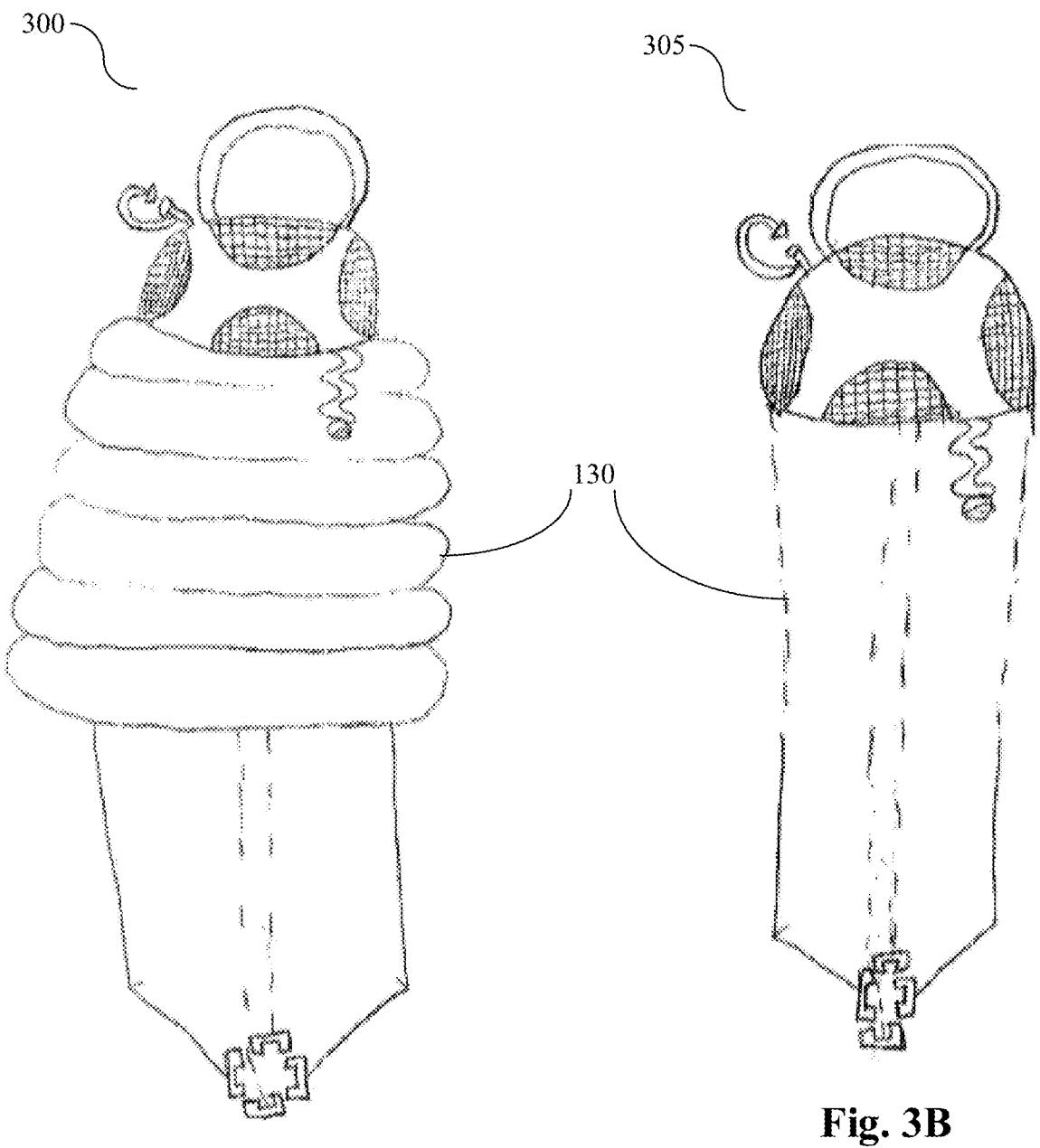
FIGS. 3A-3B illustrate an exemplary biological pollinization system, where
Figure 4:
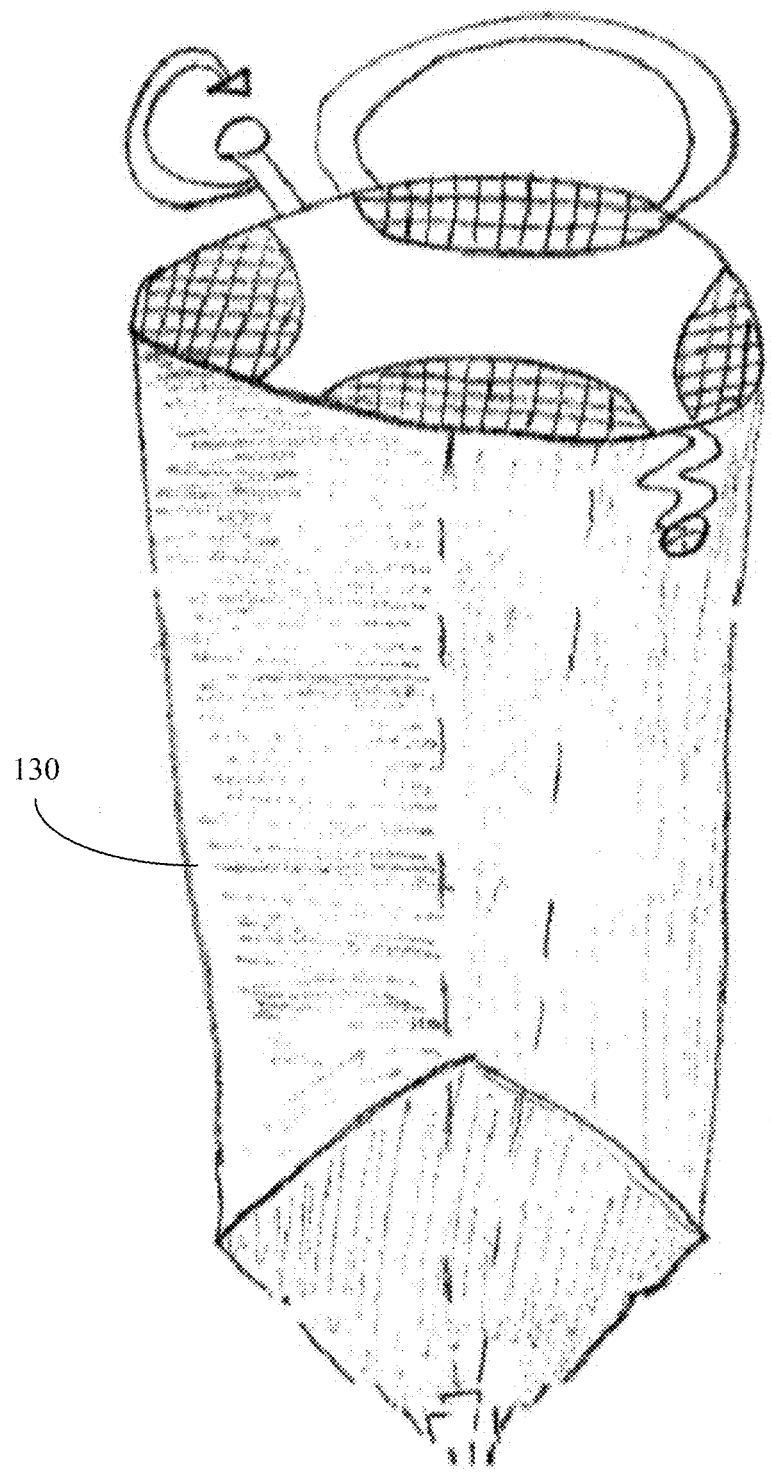
FIG. 4 illustrates an exemplary biological pollinization system, in accordance with an embodiment of the present invention.
Figure 5:
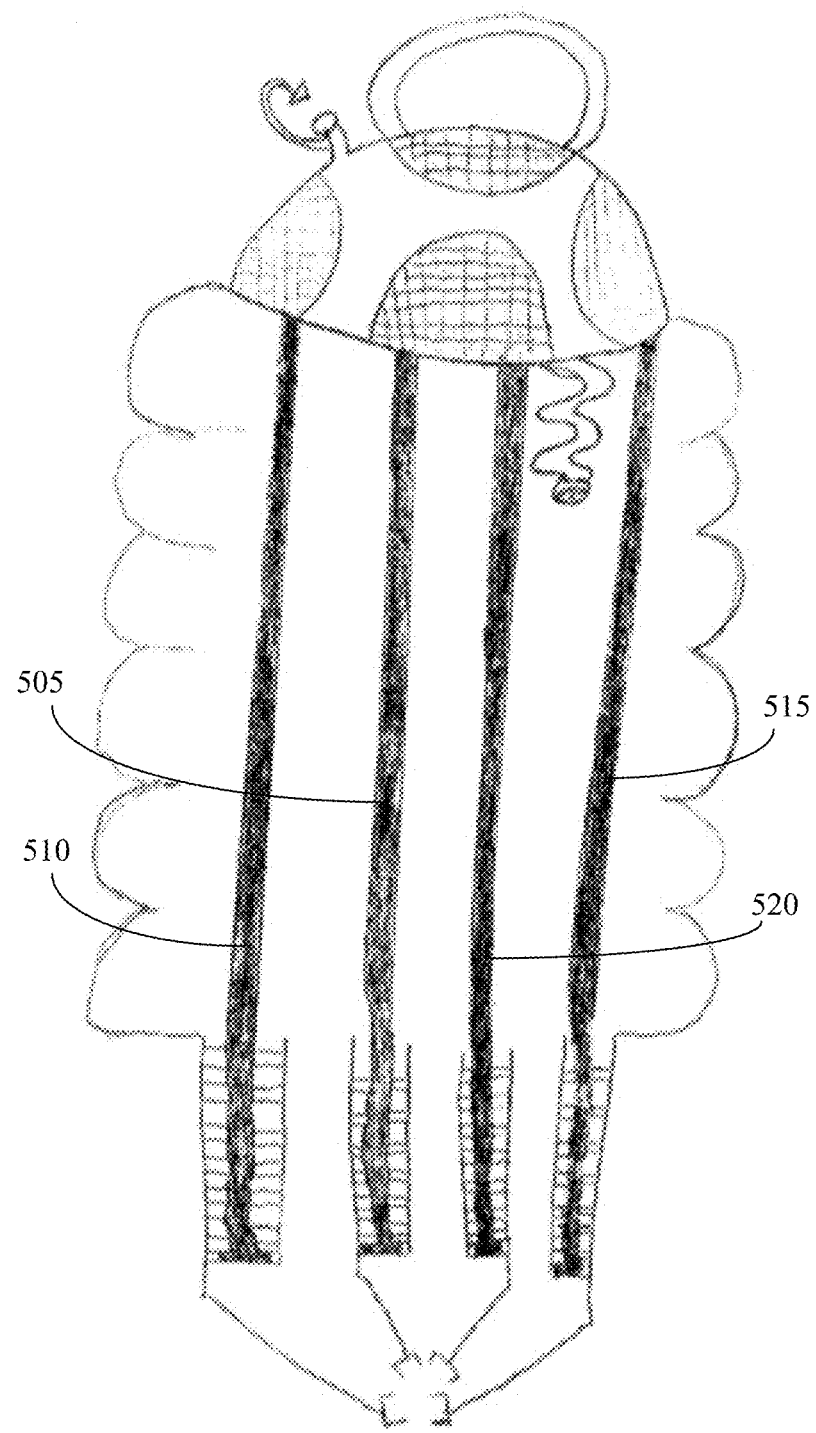
FIG. 5 illustrates an exemplary biological pollinization system with arms, in accordance with an embodiment of the present invention. With reference to both FIG. 1 and FIG. 5, arms 505-520 provide support to biological.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see *Ex parte Mallory*, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See *Energy Absorption Sys., Inc. v. Roadway*

*Safety Servs., Inc.*, Civ. App. 96-1264, slip op. at 10 (Fed. Cir. Jul. 3, 1997) (unpublished) *Hybridtech v. Monoclonal Antibodies, Inc.*, 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See *Seattle Box Co. v. Industrial Crating & Packing, Inc.*, 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See *In re Frye*, Appeal No. 2009-006013, 94 USPQ2d 1072, 1077, 2010 WL 889747 (B.P.A.I. 2010) Depending on its usage, the word "substantially" can denote either language of approximation or language of magnitude. *Deering Precision Instruments, L.L.C. v. Vector Distribution Sys., Inc.*, 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognized in case law to have the dual ordinary meaning of connoting a term of approximation or a term of magnitude. See *Dana Corp. v. American Axle & Manufacturing, Inc.*, Civ. App. 04-1116, 2004 U.S. App. LEXIS 18265, *13-14 (Fed. Cir. Aug. 27, 2004) (unpublished). The term "substantially" is commonly used by claim drafters to indicate approximation. See *Cordis Corp. v. Medtronic AVE Inc.*, 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also *Deering Precision Instruments, LLC v. Vector Distribution Sys., Inc.*, 347 F.3d 1314, 1322 (Fed. Cir. 2003); *Epcon Gas Sys., Inc. v. Bauer Compressors, Inc.*, 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, *Liquid Dynamics Corp. v. Vaughan Co.*, 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In *Cordis Corp. v. Medtronic AVE, Inc.*, 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In *Anchor Wall Systems v. Rockwood Retaining Walls, Inc.*, 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see *Deering Precision Instruments, L.L.C. v. Vector Distrib. Sys., Inc.*, 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see *Epcon*, 279 F.3d at 1031 ("The phrase 'substantially constant' denotes language of approximation, while the phrase 'substantially below' signifies language of magnitude, i.e., not insubstantial."). Also, see, e.g., *Epcon Gas Sys., Inc. v. Bauer Compressors, Inc.*, 279 F.3d 1022 (Fed. Cir. 2002) (construing the terms "substantially constant" and "substantially below"); *Zodiac Pool Care, Inc. v. Hoffinger Indus., Inc.*, 206 F.3d 1408 (Fed. Cir. 2000) (construing the term "substantially inward"); *York Prods., Inc. v. Cent. Tractor Farm & Family Ctr.*, 99 F.3d 1568 (Fed. Cir. 1996) (construing the term "substantially the entire height thereof"); *Tex. Instruments Inc. v. Cypress Semiconductor Corp.*, 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see *AK Steel Corp. v. Sollac*, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"— the ordinary meaning is that that endpoint is included.

In the present specification and claims, a goal of employment of such words of approximation, as contemplated in the foregoing, is to avoid a strict numerical boundary to the modified specified parameter, as sanctioned by *Pall Corp.* v. *Micron Separations, Inc.,* 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see *Verve LLC* v. *Crane Cams Inc.,* 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In *Andrew Corp.* v. *Gabriel Elecs. Inc.,* 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in *Ecolab Inc.* v. *Envirochem, Inc.,* 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see *Ecolab Inc.* v. *Envirochem Inc.,* 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see *Pall Corp.* v. *Micron Seps.,* 66 F.3d 1211, 1217, 36 USPQ2d 1225, 1229 (Fed. Cir. 1995); see, e.g., *Andrew Corp.* v. *Gabriel Elecs. Inc.,* 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see *Ex parte Mallory,* 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said, "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred, or induced by any pattern(s) of description, embodiments, examples, or referenced prior-art that may (or may not) be provided in the present patent.

References to "end user", or any similar term, as used herein, is generally intended to mean late-stage user(s) as opposed to early-stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of, or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like.

It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them—Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C . . . sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see *Norian Corp.* v *Stryker Corp.*, 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms.

Thus, in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components is described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Figures 6A, 6B, 6C, 6D:
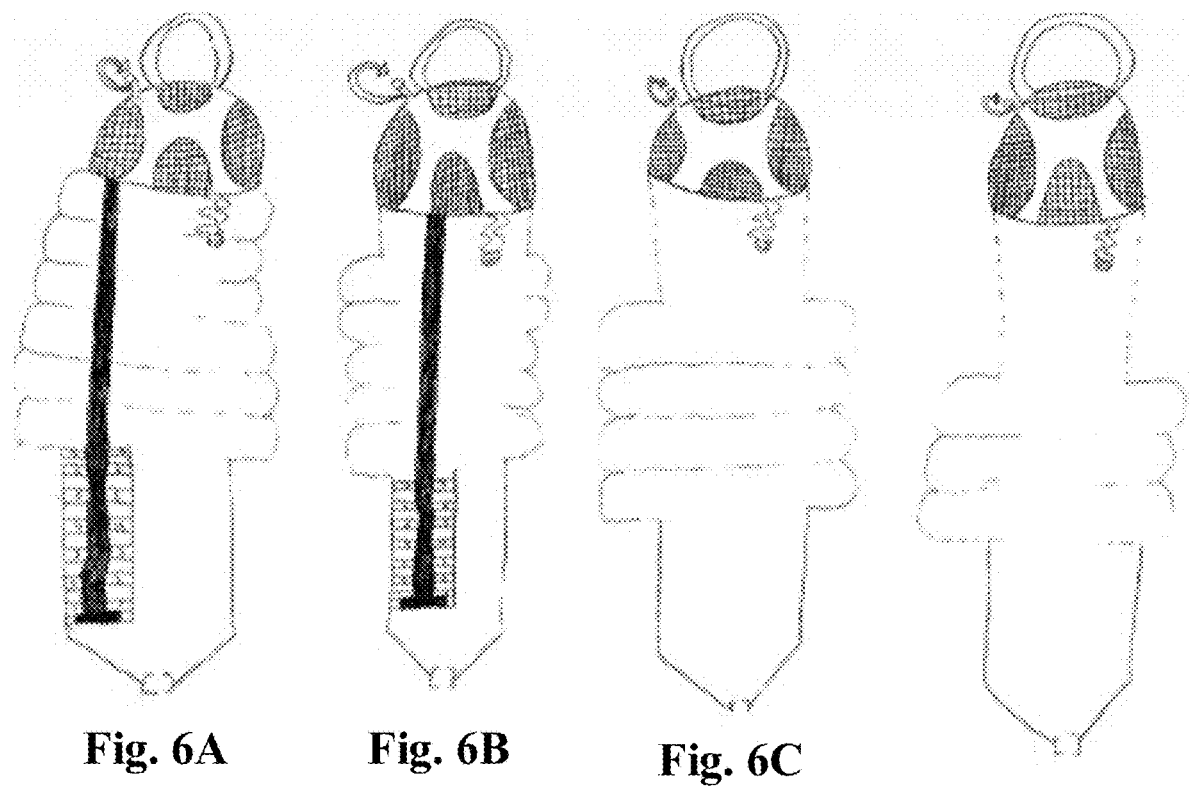
FIGS. 6A-6G illustrate different levels of elongation of an exemplary biological pollinization system, in accordance with an embodiment of the present invention.
Figures 6E, 6F, 6G:
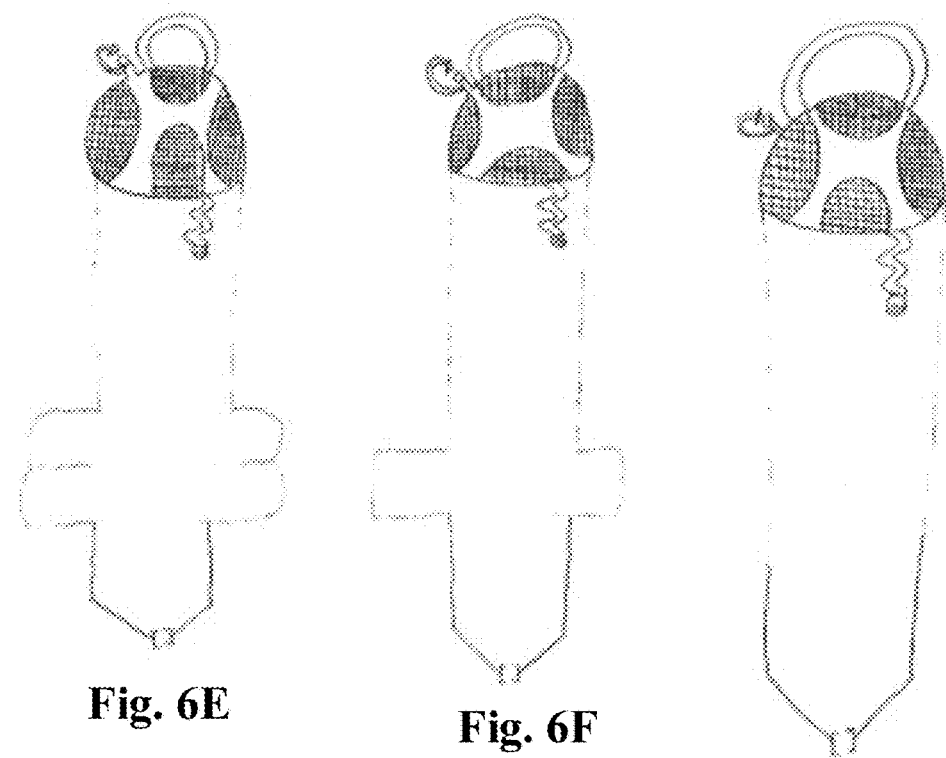

Some embodiments of the present invention and variations thereof, relate to biological pollination systems. In one embodiment of the present invention, the system may encapsulate a plant in a closed environment. Attaching using the feet of the system, to a container or to the appendage of a plant. The pollination system may expand while the plant is growing, providing ample space for the enclosed environment to flourish. The system may allow for the injection of pollen into the environment by use of a device. Filters may provide a means for the internal as well as the external environment to be contaminate free. A temperature/humidity/hygrometer gauge may align the inside of the system which may provide for adequate calculations. For the optimal growth of the environment within, a reflector may be housed around the system.

The present invention is illustrated by way of example, and not by way of limitation, in the figures of the accompanying drawings and in which like reference numerals refer to similar elements and in which:

FIG. 1 illustrates an exemplary biological pollination system, in accordance with an embodiment of the present invention. Biological pollination system 100 may comprise handle implement 105, pollinization tunnel constituent 110, pollen intake component 115, mesh filter element 120, pollen ball implement 125, expandable outer material component 130, temperature and humidity measurement device 135, guard implement 140, arm portion 145, bendable material component 150, coil tool 155, leg portion 160, feet portion 165 and tightening apparatus 170. Expandable outer material component 130 may include an accordion shape structure that may encapsulate a plant in a closed environment where the accordion shape structure provides the expandable closed environment. Temperature and humidity measurement device 135 may be attached to either the exterior or interior of outer material component 130, and may be used to monitor the temperature and humidity inside biological pollinization system 100. As will be appreciated by one skilled in the art, temperature, and humidity measurement device 135 may be implemented by any combination of apparatuses known in the art, such as, but not limited to, thermometers, hygrometers, temperature gauge, etc. Guard implement 140 may be implemented to hold bendable material component 150 in place. Guard implements may allow for the system to be raised or lowered along different intervals. The remaining embodiments will be described in more detail in the following figures.

FIGS. 2A-2B illustrate an exemplary pollinization head piece, in accordance with an embodiment of the present invention. Now referring to both FIG. 1 and FIG. 2A, pollinization head piece 200 may include handle 105, which may be used to transport and elongate biological pollinization system 100. Pollen may be inserted into biological pollinization system 100 via pollen intake component 115. While pollen intake component 115 is not in use, stopper constituent 210, which may be attached to pollen intake component 115, may be inserted into pollen intake component 115 to create an airtight seal, and prevent contaminants from entering biological pollinization system 200. To allow air to flow in and out of biological pollinization system 100, sections of pollinization head piece may be comprised of mesh filter element 120, at the same time may be used to keep contaminants and unwanted pollen out of biological pollinization system 100. Mesh filter element 120 may include woven metal wire or plastic strands which may stop particles that are too large from passing through openings in the mesh which allow air to flow in and out of biological pollinization system 100. FIG. 2B illustrates an internal view of pollinization head piece 200. Now referring to both FIG. 1 and FIG. 2B, after pollen enters the system via pollen intake component 115, pollen may enter pollinization tunnel 110 and be distributed throughout biological pollinization system 100 via pollen ball implement 125. To ensure that contaminants do not enter biological pollinization system 100, disinfecting guards 205 may line pollinization tunnel 110, and may be used to clean the nose or tip of pollen delivery devices to be used with the system.

FIGS. 3A-3B illustrate an exemplary biological pollinization system, where FIG. 3A shows the exemplary biological pollinization system while compressed and FIG. 3B shows the exemplary biological pollinization system while expanded, in accordance with an embodiment of the present invention. Biological pollinization system 100 may be used during the entire lifetime of a plant, and may elongate to accommodate for plant growth. With reference to both FIG. 1 and FIG. 3A, biological pollinization system 100 may be compressed during the early stages of plant growth or when encompassing a shorter plant. In this case, outer material component 130 may be compacted, bringing the upper portion of biological pollinization system 100 closer to the plant itself and taking up less space. With reference to both FIG. 1 and FIG. 3B, biological pollinization system 100 may also be elongated during the later stages of plant growth or when encompassing a taller plant. In this case, outer material component 130 may be elongated to provide more room for the plant as needed.

FIG. 4 illustrates an exemplary biological pollinization system, in accordance with an embodiment of the present invention. With reference to both FIG. 1 and FIG. 4, outer material component 130 may be used to contain pollen within biological pollinization system 100 while keeping out contaminants. As will be appreciated by one skilled in the art, adjustable outer material component 130 may be made of various materials, such as, without limitation, kraft paper, canvas, glassine, plastic, polyester, micro-mesh, Polyethylene, Polyvinyl Chloride, Rubber, Polypropylene, Polystyrene, Thermoplastic, Cotton Fiber Bags, Thermosetting Plastics, etc.

FIG. 5 illustrates an exemplary biological pollinization system with arms, in accordance with an embodiment of the present invention. With reference to both FIG. 1 and FIG. 5, arms 505-520 provide support to biological pollinization system 100 by acting as the foundation for the expansion of the system. Guard implements 140 are attached to arms 505-520, and bendable material components 150 rest inside guard implements 140. While four arms are depicted, it will be appreciated by one skilled in the art that greater or fewer arms may be used to provide support for biological pollinization system 100.

FIGS. 6A-6G illustrate different levels of elongation of an exemplary biological pollinization system, in accordance with an embodiment of the present invention. Biological pollinization system 100 may be expanded to different levels of elongation, elevation, and/or expansion while the plant grows and to accommodate for different sizes of plants. FIG. 6A depicts biological pollinization system 100 in stable form while fully compressed. In many cases, biological pollinization system 100 may begin in this stage while the plant is at its shortest height and may provide adequate space for the plant to grow. FIGS. 6B-6F demonstrate elongation levels 1-5, respectively, and show the different stages of biological pollinization system 100. Finally, FIG. 6G depicts biological pollinization system 100 at elongation level 6, while it is fully expanded. As will be appreciated by one skilled in the art, although 6 elongation levels are depicted, fewer or greater elongation levels may be used with biological pollinization system 100.

Figure 7A:
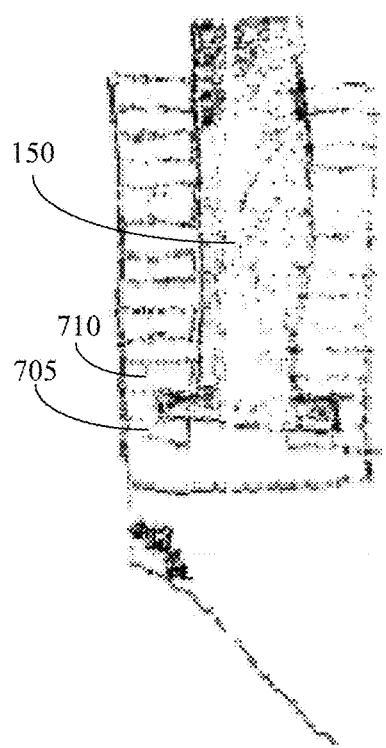
FIG. 7A-7C illustrate the arm movement that may occur during the elongation of an exemplary biological pollinization system, in accordance with an embodiment of the present invention.
Figure 7B:
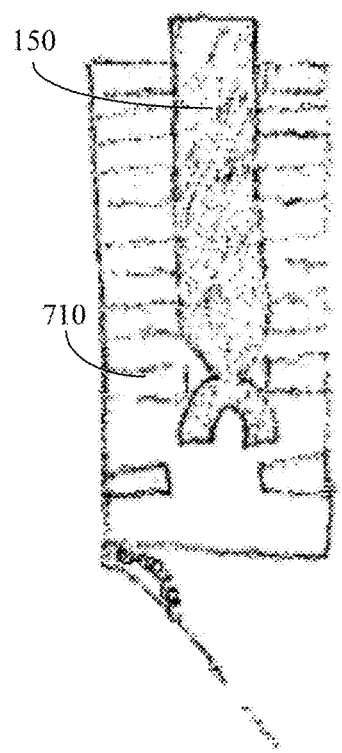
Figure 7C:
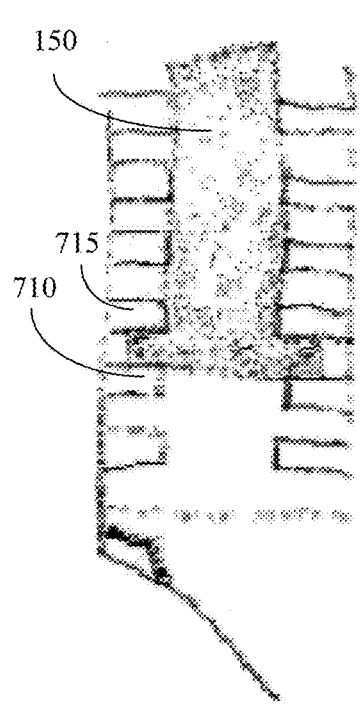

FIG. 7A-7C illustrate the arm movement that may occur during the elongation of an exemplary biological pollinization system, in accordance with an embodiment of the present invention. While biological pollinization system 100 elongates to different levels, bendable material 150 may assist in elongation or compression of the system as bendable material 150 may move according to the different elongation levels. With reference to both FIG. 7A and FIG. 1, bendable material 150 is in elongation level 1 and is caught stably between a first guard 705 and a second guard 710. Guards 705 and 710 hold bendable material 150 in place, and may enable the system to be raised or lowered along different intervals. With reference to both FIG. 7B and FIG. 1, biological pollinization system 100 is now being transitioned from elongation level 1 to elongation level 2. To do so, the user must simply pull up on handle 105 (not shown), causing bendable material 150 to push up against second guard 710 and start to slide past second guard 710. With reference to both FIG. 7C and FIG. 1, after bendable material 150 slides past second guard 710, it may be caught in-between second guard 710 and third guard 715. Bendable material 150 is now securely in place, and biological pollinization system 100 has successfully been transitioned into elongation level 2. A similar process may be used to transition biological pollinization system 100 between any of the adjacent levels.

Figure 8:
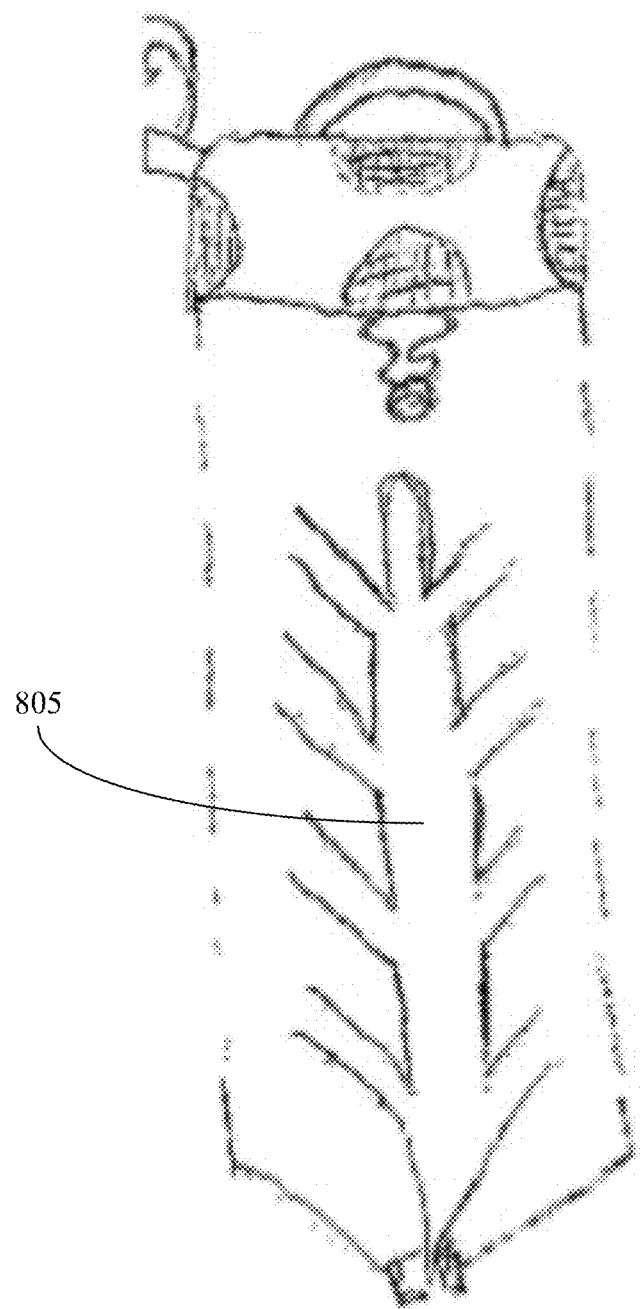
FIG. 8 illustrates an exemplary biological pollinization system encapsulating an exemplary pollinating plant, in accordance with an embodiment of the present invention.

FIG. 8 illustrates an exemplary biological pollinization system encapsulating an exemplary pollinating plant, in accordance with an embodiment of the present invention. While fully expanded, biological pollinization system 100 may encapsulate pollinating plant 805, providing an adequate environment for pollination.

Figure 9A:
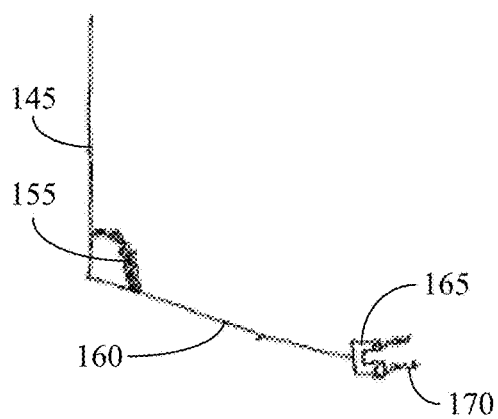
FIGS. 9A-C illustrate the outward leg movement of an exemplary biological pollinization system, in accordance with an embodiment of the present invention.
Figure 9B:
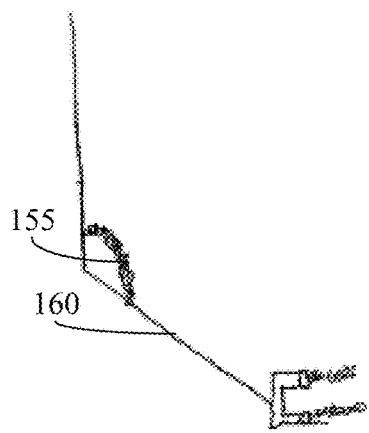
Figure 9C:
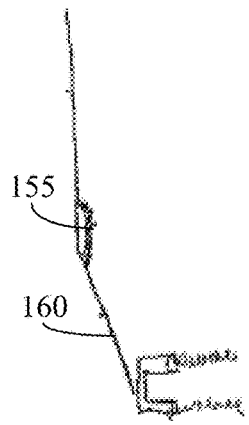

FIGS. 9A-C illustrate the outward leg movement of an exemplary biological pollinization system, in accordance with an embodiment of the present invention. With reference to both FIG. 1 and FIG. 9A, arm portion 145 and leg portion 160 provide support for biological pollinization system 100, and may comprise any material known in the art, such as, but not limited to, aluminum, wood, plastic, copper, etc. Coil tool 155 is attached to both arm portion 145 and leg portion 160, and provides tension while leg 160 moves towards a vertical orientation with respect to arm 145, as will be described below. Foot portion 165 may be attached opposite arm portion 145 on leg portion 160, and serves as an attachment point at the base of biological pollinization system 100. Foot portion 165 may be composed of a hollow material, in which tightening apparatus 170 resides. Tightening apparatus 170 may be made of a coil which severely contracts and or tightens after expansion. The coil which lay inside the feet of the system is meant to expand and conform back into its original shape thus tightening around container or appendage of plant. In the preferred embodiment, there may be four feet to provide stability to the overall system but, as will be appreciated by one skilled in the art, greater or fewer feet is still considered within the scope of the invention. Leg portion 160 may move about the joint in-between leg portion 160 and arm portion 145 towards a vertical position, allowing the base of biological pollinization system 100 to expand outward and provide an opening in which a plant may enter. With reference to both FIG. 1 and FIG. 9B, leg portion 160 may move into a more vertical position while it expands outward, straightening coil 155 to accommodate. With reference to both FIG. 1 and FIG. 9C, leg portion 160 may move into an even more vertical position, further straightening coil 155 to accommodate for the range of movement.

Figure 10A:
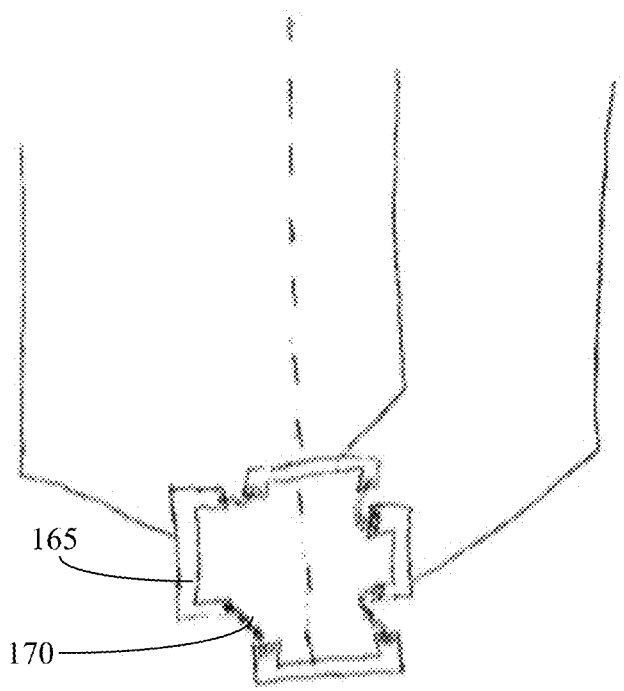
Figure 10B:
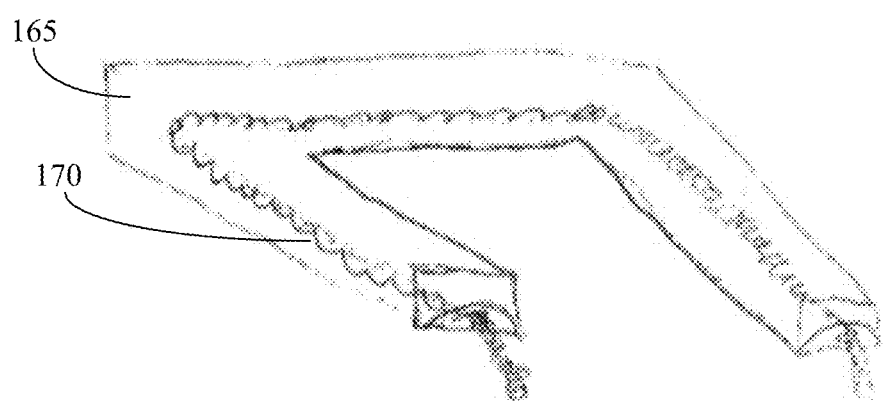

FIGS. 10A-10B illustrate exemplary feet of a biological pollinization system, wherein FIG. 10A shows the interlocking of the exemplary feet and FIG. 10B shows an exemplary foot, in accordance with an embodiment of the present invention. With reference to both FIG. 1 and FIG. 10A, feet portion 165 may be interlocked with each other via tightening apparatus 170, creating an airtight seal at the base of a plant encapsulated by biological pollinization system 100. With reference to FIG. 1 and FIG. 10B, the internal structure of feet portion 165 may be seen. As shown, feet portion 165 may be hollow and may contain tightening apparatus 170 internally.

Figure 11A:
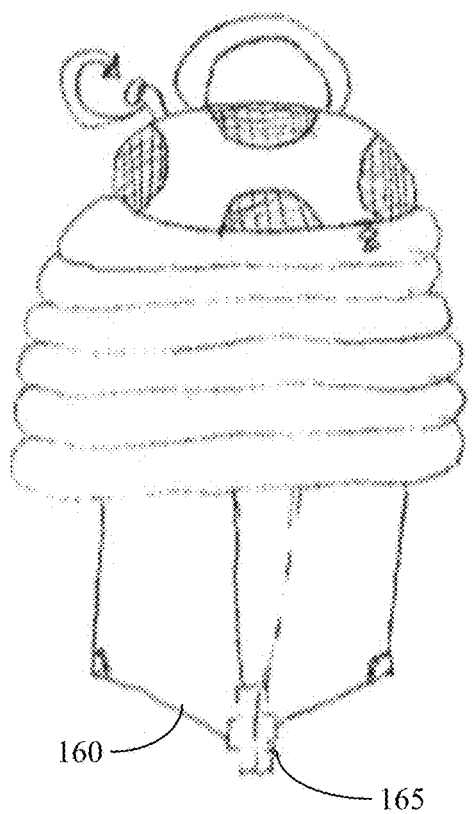
FIGS. 11A-11B illustrate the outward leg movement of an exemplary biological pollinization system, in accordance with an embodiment of the present invention.
Figure 11B:
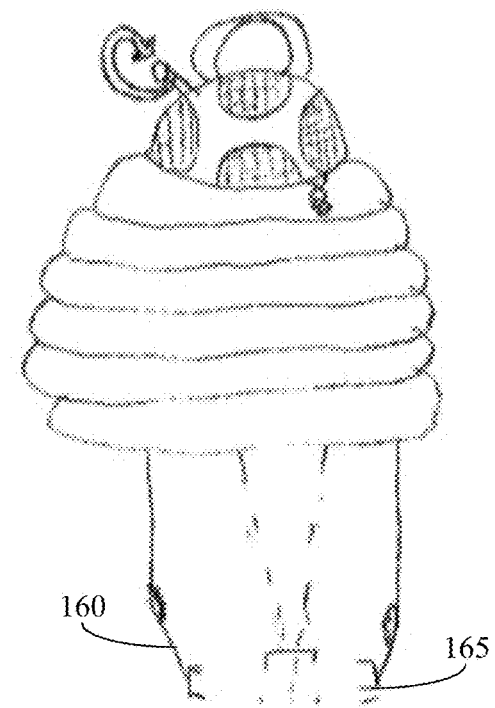
Figures 15A, 15B:
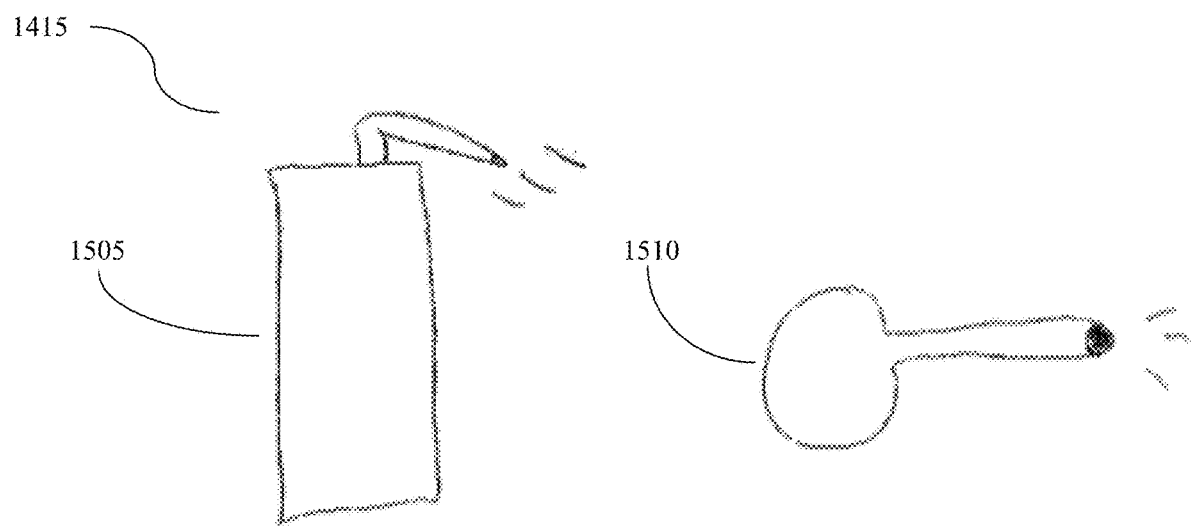
FIGS. 15A-15B illustrate exemplary pollen delivery devices, in accordance with an embodiment of the present invention.
Figure 16:
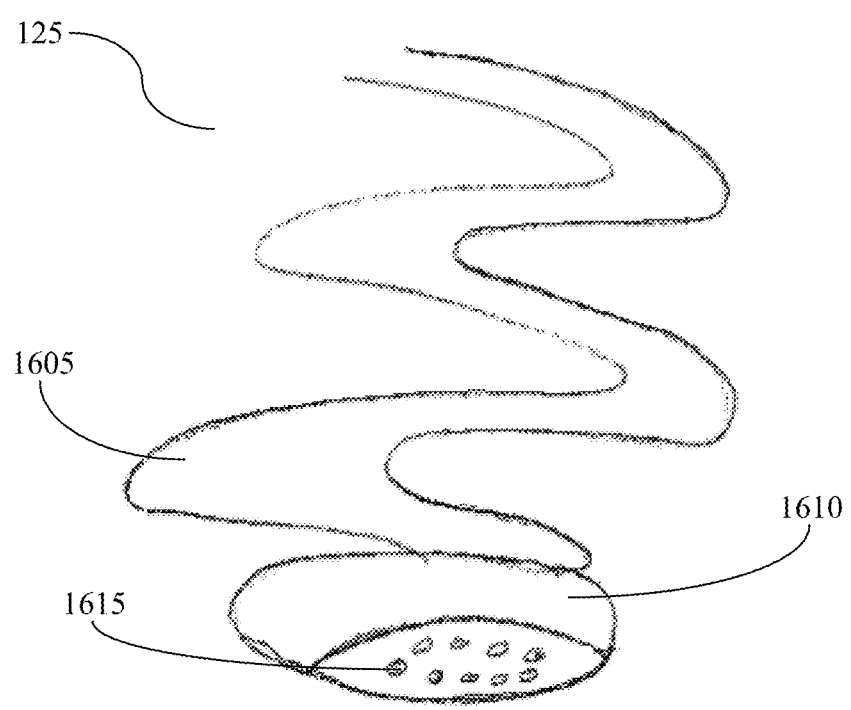
FIG. 16 illustrates an exemplary pollen ball, in accordance with an embodiment of the present invention.
Figure 17:
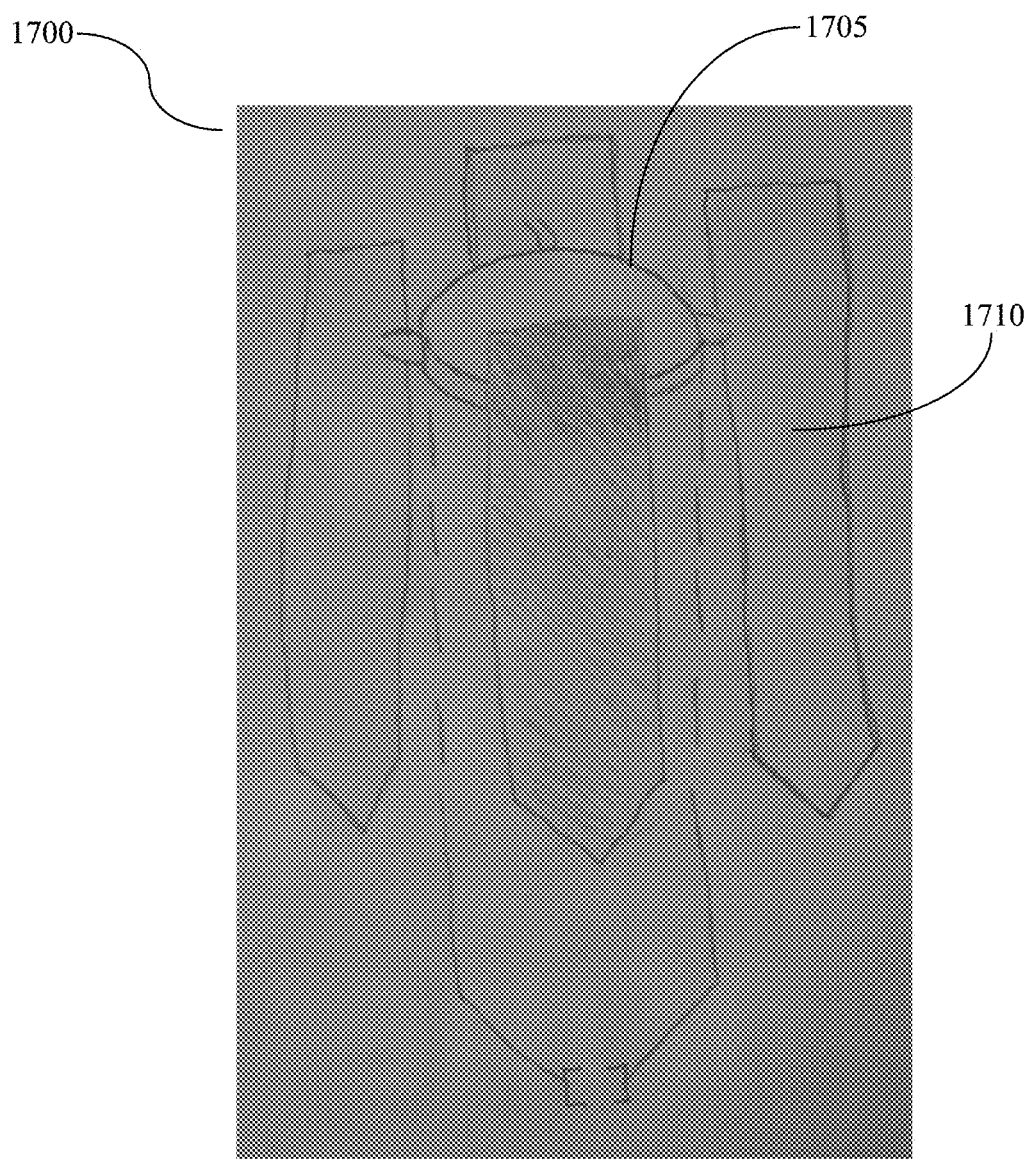
FIG. 17 illustrates an exemplary reflector, in accordance with an embodiment of the present invention.
Figure 18A:
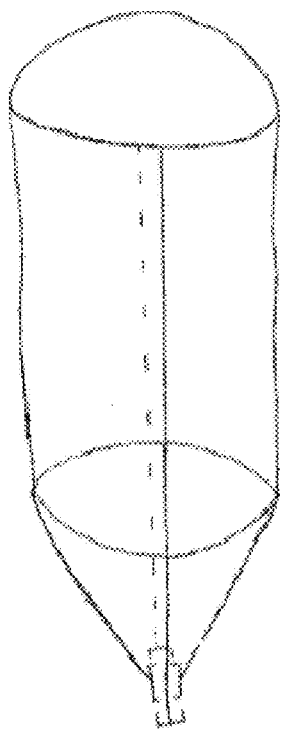
FIGS. 18A-18E illustrate alternative variations of an exemplary biological pollinization system, in accordance with an embodiment of the present invention.
Figure 18B:
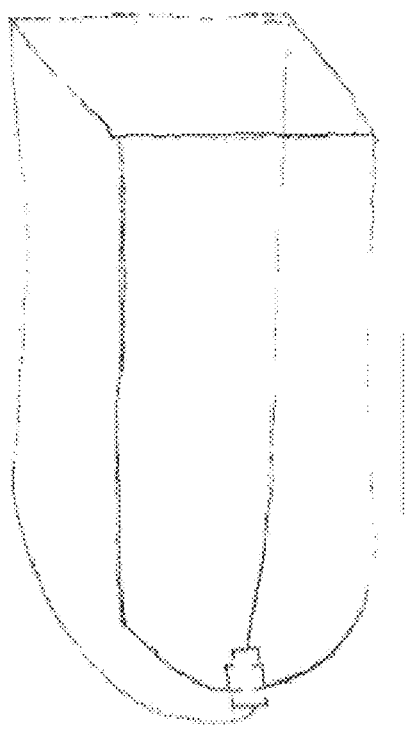
Figure 18C:
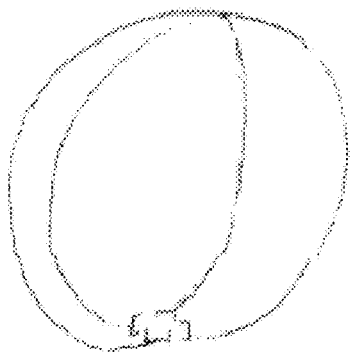
Figure 18D:
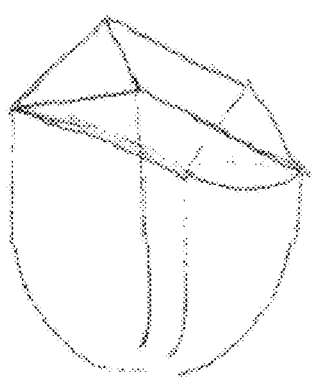
Figure 18E:
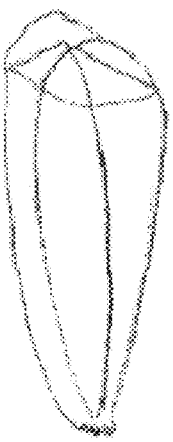

FIGS. 11A-11B illustrate the outward leg movement of an exemplary biological pollinization system, in accordance with an embodiment of the present invention. With reference to FIG. 1 and FIG. 11A, legs 160 may be in an almost horizontal position while biological pollinization system 100 is in a stable form, with feet portion 165 in a closed position. Typically, biological pollinization system 100 may be in stable form while it encompasses a plant or during transport. With reference to FIG. 1 and FIG. 11B, legs 160 may be in an almost vertical position while biological pollinization system 100 is in an unstable form, with feet portion 165 in an open position. Typically, biological pollinization system 100 may be in unstable form when biological pollinization system 100 is to be placed over a plant, or while biological pollinization system 100 is attached to a base, as will be described in greater detail below.

FIGS. 12A-12B illustrate an exemplary biological pollinization system placed over a plant in a base, in accordance with an embodiment of the present invention. With reference to FIG. 1 and FIG. 12A, biological pollinization system 100 may be expanded horizontally with feet portion 165 apart from each other as to accommodate for plant 1205 and circular base 1210. With reference to both FIG. 1 and FIG. 12B, feet portion 165 may fit into mounting holes 1215 of circular base appliance 1210, creating an airtight seal with circular base 1210, fully encapsulating plant 1205.

FIGS. 13A-13D illustrate exemplary base appliances to be used with an exemplary biological pollinization system, wherein FIGS. 13A-13B show exemplary base appliances and FIGS. 13C-13D show the exemplary base appliances attached to the exemplary biological pollinization system, in accordance with an embodiment of the present invention. With reference to FIGS. 12A-12B and FIGS. 13A-13B, in the preferred embodiment, bases may be of several different shapes, such as, but not limited to, circular as shown by circular base appliance 1210 or rectangular, such as rectangular base appliance 1305. As will be appreciated by one skilled in the art, bases are not limited to these two shapes, and may take up any shape, such as, but not limited to, octagonal, square-shaped, triangular, etc. Regardless of the shape, bases preferably comprise mounting holes 1215, side drainage holes 1315, and bottom drainage holes 1320. Mounting holes 1215 may provide an airtight seal and mounting points for biological pollinization system 100. Although mounting holes 1215 are depicted as rectangular, they may be of any shape, such as, but not limited to, circular, square-shaped, etc. Side drainage holes 1315 and bottom drainage holes 1320 act as a drainage for the release of waste from the system. It should be appreciated by one skilled in the art that, although four side drainage holes 1315 and four bottom drainage holes 1320 are depicted, fewer or greater of each type of drainage hole are still within the scope of the invention. With reference to FIGS. 13A-13D, biological pollinization system 100 may be adapted to fit securely on both base types, as shown in FIG. 13C with biological pollinization system 100 secured to rectangular base 1305, and as shown in FIG. 13D, with biological pollinization system 100 secured to circular base 1210.

FIGS. 14A-14E illustrate an exemplary biological pollinization system in use, in accordance with an embodiment of the present invention. With reference to FIG. 1, FIG. 13A, and FIGS. 14A-14E, Initially, biological pollinization system 100 is secured to rectangular base 1305, which contains vegetative plant 1405. Vegetative plant 1405 may comprise a plant that has not yet bloomed to flower. Note that biological pollinization system 100 is in stable form, with adjustable outer material component 130 compressed, as vegetative plant 1405 does not yet require the additional height that may be provided by elongating biological pollinization system 100. As vegetative plant 1405 continues to grow, it may require more room, and as such, biological pollinization system 100 may be elongated to accommodate for this growth, as shown in FIG. 14B. As vegetative plant continues to grow, it may be desirable to secure biological pollinization system 100 onto pollinating section 1410, preventing undesirable cross pollinization from occurring and providing for a controlled environment for growth, as shown in FIG. 14C. As vegetative plant further continues to grow, biological pollinization system 100 may be expanded to accommodate for this growth by elongating material component 130. Further, pollen may be injected into biological pollinization system 100 via pollen intake 115 using a pollen delivery device 1415, such as, but not limited to, aerosol can 1505 or squeeze pump 1510 (see FIG. 15B), as shown in FIG. 14D, to produce a pollinating plant 1420. Pollinating plant 1420 may comprise vegetative plant 1405 that has received pollen. Finally, seeds 1425 may be produced by pollinating plant 1420 as a result of careful pollinization practices, as shown in FIG. 14E.

FIGS. 15A-15B illustrate exemplary pollen delivery devices, in accordance with an embodiment of the present invention. With reference to FIG. 14D and FIG. 15A, aerosol can 1505 may be used to inject pollen into biological pollinization system 100. With reference to FIG. 15B, squeeze pump 1510 may additionally be used to inject pollen into biological pollinization system 100. As will be appreciated by one skilled in the art, any pollen delivery system 1415 may be used with biological pollinization system 100, such as, but not limited to, aerosol cans, spray pumps, syringes, etc.

FIG. 16 illustrates an exemplary pollen ball, in accordance with an embodiment of the present invention. With reference to both FIG. 1 and FIG. 16, pollen ball 125 may be used to diffuse pollen into biological pollinization system 100. Pollen ball 125 may comprise pollen delivery tube 1605, pollen ball tip 1610, and pollen holes 1615. As pollen is injected into biological pollinization system 100, pollen may travel down pollen delivery tube 1605 to pollen ball tip 1610 and diffused throughout biological pollinization system 100 via pollen holes 1615. Pollen ball may be composed of any material such as, but not limited to, plastic, rubber, glass, etc.

FIG. 17 illustrates an exemplary reflector in accordance with an embodiment of the present invention. Reflector 1700 may be used to increase the amount of light that enters biological pollinization system 100. Reflector 1700 may comprise circular mount 1705 and reflective material 1710. Circular mount 1705 may be adapted to fit over biological pollinization system 100, and may secure reflector 1700 in place. Additionally, reflective material 1710 may reflect additional light into biological pollinization system 100. Reflective material may be composed of any material that reflects light, such as, but not limited to, glass mirror, acrylic mirror, aluminum foil, polished anodized aluminum, etc.

FIGS. 18A-18E illustrate alternative variations of an exemplary biological pollinization system, in accordance with an embodiment of the present invention. Biological pollinization system 100 may be adapted to different shapes and sizes depending on the needs of the user and the size of the plant it will encompass. With reference to FIGS. 18A-18E, for example, without limitation, biological pollinization system 100 may be conical, as in FIG. 18A, rectangular, as in FIG. 18B, spherical, as in FIG. 18C, pyramid-topped, as in FIG. 18D, or tear-shaped, as in FIG. 18E. As will be appreciated by one skilled in the art, biological pollinization system 100 may take on many shapes and sizes, and is not limited to the forms depicted in FIGS. 18A-18E.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent, or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing plant pollination systems according to the present invention will be apparent to those skilled in the art. Various aspects of the invention have been described above by way of illustration, and the specific embodiments disclosed are not intended to limit the invention to the particular forms disclosed. The particular implementation of the plant pollination systems may vary depending upon the particular context or application. By way of example, and not limitation, the plant pollination systems described in the foregoing were principally directed to a system that encapsulates a plant in a closed environment in order to pollinate a plant implementations; however, similar techniques may instead be applied to, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

Only those claims which employ the words "means for" or "steps for" are to be interpreted under 35 USC 112, sixth paragraph (pre-AIA) or 35 USC 112(f) post-AIA. Otherwise, no limitations from the specification are to be read into any claims, unless those limitations are expressly included in the claims.

What is claimed is:

1. A system comprising:
   means for encapsulating a plant in a closed environment;
   means for injecting pollen into said closed environment;
   means for expanding a space covered by said closed environment;
   means for filtering contaminants from entering said closed environment;
   means for attaching said closed environment to a plant appendage or plant container;
   means for holding or diffusing pollen inside said closed environment; and means for maximizing an amount light penetrating within said closed environment.

2. A system comprising:
an expandable outer material component, said expandable outer material component being configured to encapsulate a plant in a closed environment, wherein said expandable outer material component is further configured to be compacted to save space while not in use, expanded to initially accommodate the plant, and further expanded when adjusting for plant growth;
a pollen intake component, said pollen intake component being configured to receive pollen introduced in said closed environment;
a pollinization tunnel constituent, said pollinization tunnel constituent being configured to distribute pollen introduced through said pollen intake component;
a filter element, said filter element being configured to keep contaminants from entering said closed environment;
a feet portion, said feet portion being configured to provide an attachment point at a base of a plant being encapsulated;
a pollen ball implement, said pollen ball implement being configured to diffuse pollen into said closed environment;
a reflector tool, said reflector tool being configured to increase an amount of light that enters said closed environment; and
a handle implement, said handle implement being configured to cause said closed environment to transition from a first elongation level to a second elongation level, wherein a bendable material is configured to push up against a second guard and start to slide past said second guard for said closed environment to transition from said first elongation level to said second elongation level.

3. The system of claim 2, further comprising a bendable material component, said bendable material component being configured to provide stability to said closed environment at a plurality of elongation, elevation, or expansion levels.

4. The system of claim 3, further comprising a guard implement, in which said guard implement comprises a plurality of guards being configured to secure said bendable material component at said different elongation levels, and in which said plurality of guards including a first guard and a second guard, wherein at a first elongation level, said bendable material is provided stability between said first guard and said second guard.

5. The system of claim 2, further comprising an arm portion, said arm portion being configured to provide support for said closed environment.

6. The system of claim 2, further comprising a leg portion, said leg portion being configured to move towards a vertical orientation with respect to an arm portion to allow a base of said closed environment to expand outward and provide an opening in which the plant may enter.

7. The system of claim 2, further comprising a coil tool into engagement with an arm portion and a leg portion, wherein said coil tool is configured to provide tension while said leg portion moves towards a vertical orientation with respect to said arm portion.

8. The system of claim 7, in which said coil tool comprises a tightening apparatus, wherein said coil tool is further configured to contract and/or tighten after expansion.

9. The system of claim 2, further comprising a temperature and humidity measurement device, said temperature and humidity measurement device being configured to monitor a temperature and/or humidity inside said closed environment.

10. The system of claim 2, further comprising a plurality of disinfecting guards lining said pollinization tunnel, wherein said plurality of disinfecting guards is configured to clean a tip of a pollen delivery device.

11. The system of claim 2, further comprising a stopper constituent, wherein said stopper constituent is configured to be inserted into said pollen intake component to create an airtight seal and prevent contaminants from entering said closed environment.

12. The system of claim 2, further comprising a base appliance, said base appliance comprises mounting holes that are configured to provide mounting points for said closed environment.

13. The system of claim 12, in which said base appliance further comprises a plurality of side drainage holes that are configured to release waste from the system.

14. The system of claim 13, in which said base appliance further comprises a plurality of bottom drainage holes that are configured to release waste from the system.

15. A system comprising:
an outer material component, said outer material component comprises an expandable outer material component, wherein said expandable outer material component is configured to be compacted to save space while not in use, expanded to initially accommodate a plant in a closed environment, and further expanded to adjust for plant growth within said closed environment;
a pollen intake component, said pollen intake component being configured to receive pollen introduced in said closed environment;
a pollinization tunnel constituent, said pollinization tunnel constituent being configured to distribute the pollen introduced through said pollen intake component;
a filter element, said filter element being configured to keep contaminants from entering said closed environment;
a feet portion, said feet portion being configured to provide an attachment point at a base of a plant being encapsulated; and
a pollen ball implement, said pollen ball implement being configured to diffuse the pollen introduced into said closed environment.

16. The system of claim 15, further comprising:
a temperature and humidity measurement device, said temperature and humidity measurement device being configured to monitor a temperature and/or humidity inside said closed environment;
a bendable material component, said bendable material component being configured to provide stability to said closed environment at a plurality of elongation, elevation, or expansion levels;
a plurality of disinfecting guards lining said pollinization tunnel, wherein said plurality of disinfecting guards is configured to clean a tip of a pollen delivery device; and
a reflector tool, said reflector tool being configured to increase an amount of light that enters said closed environment.

17. The system of claim 16, further comprising a guard implement, in which said guard implement comprises a plurality of guards being configured to secure said bendable material component at said different elongation levels, and in which said plurality of guards including a first guard and a second guard, wherein at a first elongation level, said bendable material is provided stability between said first guard and said second guard.

18. The system of claim 17, further comprising a handle implement, said handle implement being configured to cause said closed environment to transition from said first elongation level to a second elongation level, wherein said bendable material is configured to push up against said second guard and start to slide past second guard for said closed environment to transition from said first elongation level to said second elongation level.

19. The system of claim 18, further comprising:
- an arm portion, said arm portion being configured to provide support for said closed environment;
- a leg portion, said leg portion being configured to move towards a vertical orientation with respect to said arm portion to allow a base of said closed environment to expand outward and provide an opening in which the plant may enter;
- a coil tool into engagement with said arm portion and leg portion, wherein said coil tool is configured to provide tension while said leg portion moves towards a vertical orientation with respect to said arm portion; and
- in which said coil tool comprises a tightening apparatus, wherein said coil tool is further configured to contract and/or tighten after expansion.

\* \* \* \* \*